United States Patent [19]

Witucki et al.

[11] 4,168,273

[45] Sep. 18, 1979

[54] METHOD FOR THE PREPARATION OF GLYCIDYL 2,2-DINITRO-2-FLUOROETHOXIDE

[75] Inventors: Edward F. Witucki, Van Nuys; Milton B. Frankel, Tarzana, both of Calif.

[73] Assignee: The United States of America as represented by the Secretary of the Air Force, Washington, D.C.

[21] Appl. No.: 452,228

[22] Filed: Mar. 14, 1974

[51] Int. Cl.$^2$ ............................................. C07D 301/28
[52] U.S. Cl. .............................. 260/348.14; 149/19.3; 149/88; 260/348.45
[58] Field of Search ......... 149/88; 260/348 R, 348.14, 260/348.45

[56] References Cited

U.S. PATENT DOCUMENTS

| 3,636,060 | 1/1972 | Frankel et al. ................. 260/348.14 |
| 3,652,600 | 3/1972 | Grakauskas ....................... 260/348 R |
| 3,784,420 | 1/1974 | Frankel et al. ..................... 149/88 X |

Primary Examiner—Leland A. Sebastian
Attorney, Agent, or Firm—Joseph E. Rusz; William J. O'Brien

[57] ABSTRACT

A method for synthesizing glycidyl 2,2-dinitro-2-2 fluoroethoxide which comprises adding sodium hydroxide to a reaction mixture of epibromohydrin and 2,2-dinitro-2-fluoroethanol in the presence of carbon tetrachloride as a solvent for the reaction mixture.

1 Claim, No Drawings

METHOD FOR THE PREPARATION OF GLYCIDYL 2,2-DINITRO-2-FLUOROETHOXIDE

BACKGROUND OF THE INVENTION

This invention relates to a method for preparing glycidyl 2,2-dinitro-2-fluoroethoxide. More particularly, this invention concerns itself with a method which provides for the convenient practical and safe synthesis of 2,2-dinitro-2-fluoroethoxide.

As the utilization of propellants and propellant systems increases, the problem of producing and handling propellant materials with a reasonable degree of safety has evoked considerable interest. A great deal of research and effort has been expended in an attempt to deal with this problem and improve safety conditions. One of the materials which finds wide application in the propellant field is glycidyl 2,2-dinitro-2-fluoroethoxide. It is an energetic, dense, thermally stable monomeric material which can be easily converted to dihydroxy-terminated prepolymers. These prepolymers can be mixed with conventional propellant ingredients and then cast cured into explosive or propellant systems.

The most direct route to the synthesis of glycidyl 2,2-dinitro-2-fluoroethoxide is through the reaction of epibromohydrin and 2,2-dinitro-2-fluoethanol. However, this reaction is extremely dangerous and is considered to be in the Class A explosive category. The handling of the reactants and the resultant reaction products therefore poses a serious problem of safety for personnel involved in synthesising the monomers of this invention.

In attempting to overcome the problems and hazardous conditions associated with the prior art method, it has been found that the inclusion of carbon tetrachloride as a reaction solvent desensitizes the reaction mixture, making it non-hazardous. As a consequence, the reaction is removed from the Class A explosives category.

SUMMARY OF THE INVENTION

In accordance with this invention, it has been found that glycidyl 2,2-dinitro-2-fluoroethoxide can be synthesized in a simple economical and a non-hazardous manner by a one step process. The process involves the use of carbon tetrachloride as a solvent for the conventional 1:1 reaction mixture of epibromohydrin and 2,2-dinitro-2-flouroethanol. The reaction induced by mixing epibromohydrin and 2,2-dinitro-2-fluoroethanol in a 1:1 ratio in the presence of sodium hydroxide is well known as the most direct and conventional means for producing the monomeric material of this invention. However, the reaction is extremely dangerous and of such a sensitivity that it is categorized as Class A explosive. The inclusion of carbon tetrachloride, however, as a solvent for the reaction renders it safe to a degree that removes it from the Class A explosive category.

Accordingly, the primary object of this invention is to provide a non-hazardous method for the synthesis of glycidyl-2,2-dinitro-2-fluoroethoxide.

Another object of this invention is to provide a one step reaction process for the preparation of glycidyl-2,2-dinitro-2-fluoroethoxide that includes the use of carbon tetrachloride as a reaction solvent.

Still another object of this invention is to provide a means for de-sensitizing the reaction mixture of epibromohydrin and 2,2-dinitro-2-fluoroethanol to a degree that justifies its removal from a Class A explosive category.

The above and still other objects and advantages of the present invention will become more readily apparent upon consideration of the following detailed description thereof.

DESCRIPTION OF THE PREFERRED EMBODIMENT

Pursuant to the above objects, the present invention concerns itself with a method for synthesizing glycidyl 2,2-dinitro-2-fluoroethoxide, herein after referred to as GDNFE.

GDNFE is an energetic, dense, thermally stable monomer and has been converted to dihydroxy-terminated liquid propolymers. These prepolymers can be mixed with energetic plasticizers such as bis(fluorodinitroethyl) formal, loaded with oxidizers such as HMX, RDK, ammonium perchlorate and fuels such as aluminum and cast cured into thermally stable, dense, energetic explosive or propellant systems. Because of the great promise of GDNFE for improved thermally stable, dense, energetic explosive and propellant formulations, it was highly desirous of developing a simple, economical and especially safe procedure for the production of GDNFE.

The most direct route to the synthesis of GDNFE is by the one-step reaction of epibromohydrin (EHB) and 2,2-dinitro-2-fluoroethanol (FDNE) in the presence of sodium hydroxide. This reaction is exemplified best by referring to the following equation:

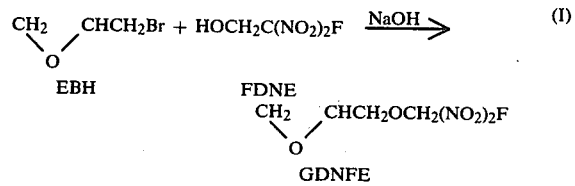

It has been found that the 1:1 mixture of the reactants (EBH and FDNE) is of such sensitivity as to place it in the Class A explosive category. The mixture at reaction's end which contains EBH, FDNE, GDNFE and high boiling by-products is also a Class A explosive.

It has further been found that the inclusion of CCl$_4$ as a reaction solvent de-sensitizes these mixtures making them non-hazardous and removes them from the Class A explosives. The yield of GDNFE in the CCl$_4$ system is comparable to that of the non-solvent system.

Impact sensitivities were determined using the drop weight tester. The upper limit of a Class A explosive is 80 inch-lbs. The tester was calibrated with u-propyl nitrate and nitromethane which furnished 0.50 percent points of 11 and 20 inch-lbs., respectively. Preliminary data on the GDNFE reaction mixtures is given below in Table I.

TABLE I

| | sensitivity |
|---|---|
| Before reaction: | |
| non-solvent system | 70 inch-lbs. |
| 35 % CCl$_4$ | 100 inch-lbs. |
| 55% CCl$_4$ | 100 inch-lbs. |
| After reaction: | |
| non-solvent system | 80 inch-lbs. |
| 20–55% CCl$_4$ | 100 inch-lbs. |

The conversion and yields of GDNFE prepared in CCl$_4$ were determined for 1,2 and 3 days at 0° C. The results are listed below in Table II.

TABLE II

PREPARATION OF GDNFE IN CCl$_4$ at 0° C.

| | Conversion % | Yield % |
|---|---|---|
| 1 day | 13–15 | 55 |
| 2 days | 18–20 | 50 |
| 3 days | 20–22 | 40 |

The presence of CCl$_4$ also makes reaction work-up easier. The reaction mixture at reaction's end contains FDNE, EBH, high boiling by-products, and GDNFE; thus, presenting a separation problem. With CCl$_4$ the quantity of FDNE in the organic phase is less than in the non-solvent system (3–5% compared to 10–15%) and the quantity of high boiling by-products formed in the reaction is lower (6% compared to 8–12%) thereby reducing the separation problem. In addition, the presence of CCl$_4$ also eases the emulsion problem encountered in the washing steps of work-up. The specific practice of the invention will be more completely understood by reference to the following example.

EXAMPLE

A solution of 30 g. (0.25 mole) of FDNE, 34 g. (0.25 mole) of EBH in 58 milliliters of CCl$_4$ containing 1% (by wt.) of triton X-100 was cooled to 0° C. Water (65 milliliters) was added and with vigorous stirring 53.5 milliliters of 16% sodium hydroxide was added dropwise maintaining the temperature at 0° C. The reaction mixture was then stirred at 0° C. for 24 hours. The layers were separated and the organic portion was washed four times with dilute NaOH and twice with H$_2$O. The quantity of CCl$_4$ was doubled and the solution was passed through a small silicon gel column. Solvent (CCl$_4$) and EBH were removed by means of a Rince evaporator. Pure GDNFE (7.9 g., 15% conversion) was isolated by distillation through a falling film Rota Still.

While the invention has been described with particularity in reference to a specific embodiment thereof, it is to be understood that the disclosure of the present invention is for the purpose of illustration only and it is not intended to limit the invention in any way, the scope of which is defined by the appended claims.

What is claimed is:

1. A method for the production of glycidyl 2,2-dinitro-2-fluoroethoxide which consists essentially of the step of adding sodium hydroxide to a solvent solution mixture containing (a) about 20 to 55 weight percent carbon tetrachloride and (b) the balance being substantially all a 1:1 mole ratio mixture of epibromohydrin and 2,2-dinitro-2-fluoroethanol to effect a reaction therebetween and separating the reaction product.

* * * * *